(12) United States Patent
Heydrich et al.

(10) Patent No.: US 6,713,656 B2
(45) Date of Patent: Mar. 30, 2004

(54) PREPARATION OF DIACETALS OF GLYOXAL

(75) Inventors: Gunnar Heydrich, Limburgerhof (DE); Nicola Christiane Aust, Mannheim (DE); Hermann Pütter, Neustadt (DE); Andreas Fischer, Ludwigshafen (DE); Jörg Botzem, Limburgerhof (DE)

(73) Assignee: BASF Aktiengesellschaft, Ludwigshafen/Rh. (DE)

( * ) Notice: Subject to any disclaimer, the term of this patent is extended or adjusted under 35 U.S.C. 154(b) by 0 days.

(21) Appl. No.: 10/262,980

(22) Filed: Oct. 3, 2002

(65) Prior Publication Data

US 2003/0069451 A1 Apr. 10, 2003

(51) Int. Cl.⁷ .............................................. C07C 43/30
(52) U.S. Cl. ...................................................... 568/603
(58) Field of Search ......................................... 568/603

(56) References Cited

U.S. PATENT DOCUMENTS

| | | | | |
|---|---|---|---|---|
| 2,194,405 A | * | 3/1940 | Purves ........................ | 568/603 |
| 2,360,959 A | * | 10/1944 | MacDowell et al. ......... | 568/603 |
| 3,806,539 A | * | 4/1974 | Kliegman et al. ........... | 560/187 |
| 5,191,127 A | * | 3/1993 | Babler ........................ | 568/591 |
| 5,426,239 A | * | 6/1995 | Dressaire et al. ............ | 568/465 |
| 6,013,842 A | * | 1/2000 | Groning et al. .............. | 568/465 |

FOREIGN PATENT DOCUMENTS

GB       559362    * 2/1944

OTHER PUBLICATIONS

Kliegman et al., Glyozal Derivatives. V. Reaction of Alcohols with Glyoxal, Feb. 1973, J. Org. Chem., vol. 38, No. 3, pp. 556–560.*

Chastrette et al. "Etude de la composition de solutions aqueuses de glyoxal en RMN–$^{13}$C" Bulletin de la Societe Chimque de France No 1–2(1983) pp. 33–40.

Kliegman et al. "Glyoxal Derivatives. V. Reaction of Alcohols with Glyoxal" J. Org. Chem. vol. 38, No. 5, (1975) pp. 556–560.

Kliegman et al. Glyoxal Derviatives. IV 2–Dimethoxymethyl–4,5–dimethoxy–1–,3–dioxolane and 2,2'–Bis(4, 5–dimethoxy–1,3–dioxolane) J. Org. Chem vol. 37 No. 8 (1972) pp. 1276–1280.

Sangsari et al. "The monoacetalization of Glyoxal: A Direct Synthesis of 2,2–dimethoxy and diethoxy ethanals" Synthetic Communications vol. 18 No. 12 (1988) pp. 1343–1348.

* cited by examiner

*Primary Examiner*—Rosalynd Keys
(74) *Attorney, Agent, or Firm*—Keil & Weinkauf

(57) ABSTRACT

A process is described for preparing diacetals of glyoxal by reacting from 40 to 75% by weight aqueous glyoxal with monohydric alcohols in the presence of an acid catalyst, which comprises leaving a liquid mixture which, at the beginning of the reaction, comprises alcohol and glyoxal in a molar ratio of at least 15:1 and also water in a concentration of not more than 8% by weight in contact with the acid catalyst until concentration in the reaction mixture of the diacetal formed reaches at least 70% of the equilibrium concentration without more than 5% by weight of the alcohol used having already been distilled off.

14 Claims, No Drawings

PREPARATION OF DIACETALS OF GLYOXAL

The present invention relates to a process for preparing diacetals of glyoxal by reacting from 40 to 75% by weight aqueous glyoxal with monohydric alcohols in the presence of an acid catalyst.

Diacetals of glyoxal, which are sometimes also referred to as tetraacetals, are interesting precursors for organic synthesis. The most important preparative method for diacetals of glyoxal is the acid-catalyzed acetalization of glyoxal using monohydric alcohols R—OH according to the following scheme:

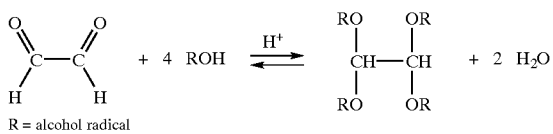

R = alcohol radical

The acid-catalyzed acetalization of glyoxal using monohydric alcohols is a complex reaction which, in addition to the monoacetal and diacetal, may also form a multitude of oligomers and/or cyclic by-products (see, for example, J. M. Kliegmann et al. in J. Org. Chem. Vol. 38 (1973) p. 556; J. Org. Chem. Vol. 37 (1972) p. 1276ff; A. Stambouli et al., Bull. Soc. Chimique France (1983) II p. 33–40.

U.S. Pat. No. 2,360,959 describes the preparation of diacetals of glyoxal from alcohols which are water-immiscible. To this end, aqueous glyoxal and a small quantity of acid catalyst are heated with at least 4 mol of the water-immiscible monohydric alcohol, an azeotropic mixture of water and alcohol is distilled off and the alcohol, after removal of the water, is recycled to the reaction. The reaction of glyoxal with methanol likewise described there is carried out in a similar way, although to separate water from alcohol, an additional, complicated fractional distillation has to be carried out. In the case of water-miscible alkanols such as methanol or ethanol, however, this process only delivers the corresponding 1,1,2,2-tetraalkoxyethane in low yields (38% in the case tetramethoxyethane).

GB 559,362 recommended the use of a water-immiscible, liquid, inert solvent such as benzene, toluene, xylene, hexane, dichloroethane or isopropyl ether in the acid catalyzed acetalization of glyoxal with monohydric alcohols. However, the use of azeotroping agents leads to additional process costs. Also, at least the halogenated azeotroping agents are toxicologically or ecologically unsafe.

F. H. Sangsari et al., Synth. Commun. 18(12) (1988) p. 1343–1348 recommended acetalization in the presence of an azeotroping agent such as chloroform using a Soxhlett apparatus filled with a drying agent to remove the water of reaction formed in preparing 1,1,2,2-tetramethoxyethane and 1,1,2,2-tetraethoxyethane.

The prior art processes for preparing diacetals of glyoxal have the disadvantage that when water-miscible alcohols such as methanol or ethanol are used, the yield of diacetal, i.e. of 1,1,2,2-tetraalkoxyethane, is low. Also, all processes require distillative measures during the conversion to remove the water of reaction which leads to increased energy and equipment costs and complicates the continuous operation of the reaction. The use of an azeotroping agent to remove the water of reaction in turn has the disadvantage that the concomitantly distilled alcohol and the azeotroping agent have to be separated.

It is an object of the present invention to provide a process for preparing diacetals of glyoxal which, even when water-miscible alcohols are used, delivers the appropriate diacetal in good yields and may be made continuous in a simple manner.

We have found that, surprisingly, this object is achieved by a process which comprises contacting a liquid mixture which, at the beginning of the reaction, comprises alcohol and glyoxal in a molar ratio of at least 15:1 and also water in a concentration of not more than 8% by weight with an acid catalyst until an approximate reaction equilibrium has been attained. According to the invention, it is believed that at least approximate reaction equilibrium has been attained when the concentration in the reaction mixture of the diacetal formed is at least 70% of the equilibrium concentration of diacetal applying to the particular composition.

Accordingly, the present invention relates to a process for preparing diacetals of glyoxal by reacting from 40 to 75% by weight aqueous glyoxal with monohydric alcohols in the presence of an acid catalyst, which comprises contacting a liquid mixture which, at the beginning of the reaction, comprises alcohol and glyoxal in a molar ratio of at least 15:1 and also water in a concentration of not more than 8% by weight with the acid catalyst until concentration in the reaction mixture of the diacetal formed reaches at least 70%, preferably at least 80%, in particular at least 90% and more preferably at least 95%, of the equilibrium concentration without more than 5% by weight of the alcohol used having already been distilled off.

The water concentration in the liquid mixture at the beginning of the reaction is preferably in the range from 2 to 8% by weight and in particular is not more than 7% by weight, for example from 3 to 7% by weight, and more preferably not more than 6% by weight, for example from 3 to 6% by weight, based in each case on the total weight of the liquid mixture. The total weight of the liquid mixture is calculated from the sum of all liquid components contained in the mixture and components dissolved therein. It does not include components which are not dissolved in the mixture such as heterogeneous catalysts. In principle, the water concentration may be adjusted in different ways:

a) for example, glyoxal can be used which has a content of at least 50% by weight and preferably at least 60% by weight. The glyoxal content of the aqueous glyoxal solution will preferably not exceed a value of 75% by weight.

b) a second possibility is to use a large excess of alcohol, for example, more than 30 mol of alcohol per mole of glyoxal, for example, from 30 to 50 mol of alcohol/mol of glyoxal in the liquid mixture.

c) a third possibility for adjusting the water content at the beginning of the reaction is adding an inert substance to the liquid mixture which is completely soluble in and/or completely miscible with the liquid mixture. When an inert substance is used, it is generally used in a quantity of at least 1% by weight, for example from 1 to 25% by weight, preferably from 2 to 20% by weight.

Preference is given to the measures a) and c), in particular a). It will be appreciated that the abovementioned measures may also be combined with each other, preferably measure a) with measure b) or measure a) with measure c).

In principle, inert substances include aprotic organic solvents and also neutral or weakly acidic salts which do not catalyze the acetalization. Preference is given to neutral or slightly acidic salts. Examples of useful salts include the halides, sulfates, nitrates, monoalkylsulfates, arylsulfonates and alkylsulfonates of metals of the first and second main group, for example, of Na, K, Li or Mg, of quaternary ammonium cations and also of iron(II) and iron(III) ions. Preferred salts include the sulfates, monoalkylsulfates, arylsulfonates and alkylsulfonates of the metals mentioned or of quaternary ammonium cations. A particular example of an alkylsulfate is methylsulfate. Particular examples of arylsulfonates include the phenylsulfonates and the tolylsulfonates. An example of an alkylsulfonate is methylsulfonate.

Examples of quaternary ammonium cations include the tetrakis-$C_1$-$C_{10}$-alkylammonium cations such as methyltriethylammonium and methyltributylammonium and also the phenyl- and benzyl-tris-$C_1$-$C_4$-alkylammonium cations such as benzyltrimethylammonium or benzyltriethylammonium.

Examples of useful salts which are sufficiently soluble in the liquid mixture and are inert under the reaction conditions, i.e. do not catalyze the acetalization, include in particular the tetrakis-$C_1$-$C_{10}$-alkylammonium alkylsulfates such as methyltriethylammonium methylsulfate and methyltributylammonium methylsulfate.

When a heterogeneous acetalization catalyst is used, in particular a strongly acidic ion exchange resin, the reaction mixture customarily contains no inert salt.

When aqueous glyoxal having a glyoxal content of at least 50% by weight and preferably at least 60 to 75% by weight is used in the process according to the invention, this is prepared by concentrating commercial aqueous glyoxal, which customarily has a glyoxal content of about 40% by weight, under reduced pressure. The aqueous glyoxal is preferably concentrated immediately before use, i.e. the concentrated aqueous glyoxal is not stored for more than 5 h, preferably not more than 2 h and in particular not more than 30 min before it is used. Concentration is preferably effected at a pressure below 500 mbar, for example from 10 to 500 mbar, preferably below 300 mbar and in particular in the range from 50 to 300 mbar. Preference is given to concentrating the aqueous glyoxal at temperatures in the range from 40 to 100° C., depending on the desired pressure and the type of vaporizer.

Preference is given to using apparatus to concentrate the aqueous glyoxal which allows a very gentle concentration process, i.e. that subject the distillation residue to very little thermal stress during concentration. In principle, useful apparatus includes that which is based on the vaporization of thin films, i.e. thin film evaporators such as falling film evaporators, blast pipe evaporators, rotary thin film evaporators, e.g. Sambay evaporators or Luwa filmtruders, and also centrifugal evaporators. Circulation evaporators such as, in particular, forced circulation evaporators, forced circulation depressurization evaporators, and also natural circulation evaporators are also suitable. Useful evaporator designs include both tube and plate apparatus. Such evaporators are well known to those skilled in the art and described, for example, in R. K. Shah and A. C. Mueller, "Heat Exchange" chapter 2.2.2.1, Ullmann's Encyclopedia of Industrial Chemistry, 6th ed. on CD-ROM, Wiley VCH.

In particular, multistage designs of the abovementioned evaporators are suitable. They may combine either identical or else different evaporators. For example, a circulation evaporator may first be used to remove a portion of the water and then a thin film evaporator may be used to adjust the desired glyoxal content. When the stages are operated at different pressure levels, the thermal energy of the vapor from the higher pressure stage may be utilized for vaporization in the lower pressure stage.

To concentrate the aqueous glyoxal, multistage separating apparatus such as countercurrent distillation columns having internals may also be used. A portion of the water may also be removed in apparatus for evaporating liquids, for example, Venturi or spray apparatus or falling film apparatus, which may be operated in cocurrent or countercurrent.

The vapors which comprise water and glyoxal traces will frequently be condensed in a condenser. What is known as vapor compression (thermal compression) by means of a vapor compressor may also be employed to utilize a portion of the thermal energy of the vapors to heat the aqueous glyoxal and at the same time to condense the water.

Stripping columns are also suitable, for example those having internals, for example, random packing, structured packing or tray columns, or those without internals, what are known as spray columns. When these types are used, concentration will be effected by introducing optionally prewarmed aqueous glyoxal at the top of this apparatus and passing in the stripping gas, preferably an inert gas, which is preferably also prewarmed, into the lower section of the column. The concentrated aqueous glyoxal solution is obtained at the bottom of the stripping column, while the water-enriched stripping gas leaves from the upper section of the apparatus. In a closed system, the moisture loading of the stripping gas can be reduced by cooling in a condenser, reheating the dried gas and passing it back into the stripping column.

In principle, all available monohydric alcohols may be used in the process according to the invention. Preference is given to alcohols whose OH group is located on a primary or secondary, preferably primary aliphatic carbon atom. Examples thereof include $C_1$-$C_{10}$-alkanols such as methanol, ethanol, n- or iso-propanol, n-, iso- or sec-butanol, n-hexanol, n-octanol, 2-ethylhexan-1-ol, $C_5$-$C_{10}$-cycloalkanols such as cyclopentanol or cyclohexanol, allylic alkanols such as allyl alcohol, arylalkanols such as phenylethanol or benzyl alcohol.

According to the invention, preference is given to the water-miscible alcohols such as methanol, ethanol, n- and isopropanol. The preparation of 1,1,2,2-tetramethoxyethane by acetalizing glyoxal with methanol is a particularly preferred embodiment of the process according to the invention.

According to the invention, the molar ratio of alcohol to glyoxal is at least 15:1 and is preferably in the range from 15:1 to 50:1 and in particular in the range from 18:1 to 30:1. Higher alcohol fractions are possible (see above), but generally require more processing.

Useful acid catalysts include both Lewis and Brönstedt acids, which, as will be known, can be used for acetalizing aldehydes. The catalysts used may be those which dissolve homogeneously in the mixture or else heterogeneous catalysts. Examples of homogeneous catalysts include, in particular, sulfuric acids and also organic sulfonic acids such as methanesulfonic acid and p-toluenesulfonic acid or sulfuric monoesters. Trichloroacetic acid or oxalic acid may likewise be used. Examples of useful heterogeneous catalysts include zirconium sulfate and also strongly acidic, in particular sulfonic acid, ion exchangers. Examples of useful acidic ion exchangers, which are used in particular in macroporous form, include ion exchangers which are sold under the brand names Lewatit®, BayKat® (Bayer AG, Leverkusen), Amberlite® and Amberlyst® (Rohm and Haas) and also Dowex® (Dow Chemicals). Examples of commercially available strongly acidic ion exchangers in macroporous form include Lewatit®S 100, Lewatit®K 2431, Lewatit®K 2621, Lewatit®K 2629, BayKat®K 2611, Amberlyst®15, Amberlyst®35 and also Dowex®50. The quantity of acid catalyst in homogeneous catalysis is generally at least 0.5% by weight, preferably at least 1% by weight and, when a heterogeneous catalyst is used, generally at least 5% by weight, in particular at least 10% by weight, based in each case on the total weight of the liquid mixture. Higher catalyst quantities are generally not disadvantageous. Particularly in heterogeneous catalysis, the catalyst quantity is limited only by the liquid volume, and the maximum catalyst quantity corresponds to a fixed catalyst bed.

In a preferred embodiment of the process according to the invention, a heterogeneous catalyst is used in the form of a fixed bed, through which the liquid mixture comprising alcohol and aqueous glyoxal is passed. The liquid mixture may be passed more than once through the fixed bed until the desired contact or residence time is attained. However, the liquid is preferably passed through the catalyst bed only once, i.e. in straight pass.

The temperatures required for acetalization are generally above room temperature and are preferably at least 50° C. and in particular are in the range from 50 to 80° C. and more preferably in the range from 65 to 75° C. The discontinuous method offers the particular possibility of working at the boiling temperature of the reaction mixture. The process according to the invention may be carried out at atmospheric pressure, at reduced or else at elevated pressure. Preference is given to carrying out the process at atmospheric pressure or at an elevated pressure of up to 5 bar.

In the process according to the invention, the reaction of glyoxal with the alcohol is carried on at least until approximate attainment of the state of equilibrium, i.e. until the concentration of the diacetal in the reaction mixture is at least 70%, preferably at least 80%, in particular at least 90% and more preferably at least 95% of the equilibrium concentration value. The time taken for the acetalization equilibrium to be attained can be quickly determined in a preceding experiment using reaction kinetics. In general, it is at least 2 and preferably at least 3 hours under the reaction conditions stated above. Frequently, equilibrium has been attained after just 10 hours. It will be appreciated that longer reaction times, e.g. up to 36 hours and preferably up to 24 hours, are also possible. Preference is given to a reaction time of from 3 to 8 hours.

After the reaction equilibrium has been attained, the acid catalyst in the case of homogeneous catalysis is deactivated in the reaction mixture by neutralizing with a suitable base such as alkali metal hydroxides or alkaline earth metal hydroxides such as NaOH, KOH or $Ca(OH)_2$, preferably neutralizing with alkali metal carbonates such as sodium carbonate or potassium carbonate or with alkali metal hydrogen carbonates such as sodium hydrogen carbonate or potassium hydrogen carbonate. In the case of heterogeneous catalysis, the catalyst is separated from the reaction mixture, for example, by filtration or, when a fixed bed catalyst is used, by decoupling the material stream from the catalyst bed.

After deactivation or removal of the acid catalyst, the liquid mixture obtained is distillatively worked up in a customary manner. In general, the excess alcohol is first distillatively removed. The alcohol distilled off is preferably reused in the next reaction batch or, in the continuous method, reintroduced to the reactor. In principle, the diacetal may be recovered and removed from coproduced monoacetal and any higher molecular weight by-products by the method described in DE-A 196 51 325. This generally involves redistilling the distillation residue remaining after distillative removal of the alcohol with the addition of water, which distills off the desired glyoxal diacetal and a large part of the water as a homoazeotrope. It has proven useful to use a portion of the water added in the form of the condensate recovered when concentrating the aqueous glyoxal, since the glyoxal contained in the condensate may be recovered in this way. The quantity of water added is preferably determined so that the total quantity of water added and the water already present in the reaction mixture exactly corresponds to the water quantity which is required for the water/glyoxal diacetal homoazeotrope. The quantity required may easily be determined by those skilled in the art using the concentrations of glyoxal and water in the reaction mixture. The distillation residue which substantially comprises the monoacetal and unconverted glyoxal, any residues of diacetal, small quantities of water and any higher oligomeric by-products may, after dewatering if necessary, likewise be recycled to the reaction.

The glyoxal diacetal may be recovered by dewatering water/glyoxal diacetal homoazeotrope resulting from the distillation in a customary manner, for example, by azeotropic distillation in the presence of the abovementioned azeotroping agents, in particular hexane, cyclohexane, heptane, octane, toluene or xylene. This procedure has the particular advantage that a complicated removal of alcohol and azeotroping agent, which is necessary in the prior art processes, is avoided.

In a preferred embodiment of the present invention, the reaction of glyoxal with the monohydric alcohol is carried out continuously using a heterogeneous, strongly acidic catalyst. This generally involves continually feeding a liquid mixture which comprises aqueous glyoxal and the monohydric alcohol and also not more than 8% by weight, preferably from 2 to 8% by weight and in particular from 3 to 7% by weight of water, into a reactor which contains a heterogeneous acid catalyst, and continuously withdrawing a liquid reaction mixture from the reactor. According to the invention, the residence time in the reactor is chosen in such a way that the concentration of the diacetal in the discharged liquid reaction mixture is at least 70%, preferably at least 80%, in particular at least 90% and more preferably at least 95% of the equilibrium concentration.

The average residence time of the reaction mixture in the reactor under the above reaction conditions is generally in the range from 2 hours to 10 hours and preferably in the range from 3 hours to 8 hours.

In principle, the remarks made above apply to the type of catalyst, the pressure and the temperature. However, preference is given to working at slightly above atmospheric pressure, e.g. from 1.1 to 5 bar. The liquid reactor effluent may likewise be worked up in the above manner.

The process according to the invention may be carried out continuously in reactors customary for continuous reaction of liquids over heterogeneous catalysts, for example in continuous stirred tank, columns or preferably in reactors having tubular geometry (tubular reactors). Preference is given to those reactors in which the heterogeneous catalyst is disposed in the form of one or more fixed beds. These include tubular reactors and columns.

According to the invention, preference is given to tubular reactors, since the acetalization equilibrium is attained particularly rapidly. Here and hereinbelow, tubular reactors include both shaft reactors (individual reaction tubes) and also tube bundle apparatus. The tubular reactors may be disposed horizontally but are preferably disposed vertically. When disposed vertically, the liquid reaction mixture may be passed either upward or else downward through the reactor.

In the tubular reactors, the heterogeneous catalyst is generally arranged in the form of one or more beds, and the reactors are generally equipped with devices which substantially prevent discharge of the catalyst during operation. The use of more than one different catalyst in structured beds is also possible.

The tubular reactors may also be equipped with internals at one or more locations through which heat may be introduced or removed. Examples of such internals include coiled tubes and horizontally or vertically disposed tubes or plates. These internals may conduct liquid or vaporous heat carriers in a controlled manner. Condensation and evaporation procedures in the reactor may also be utilized in a known manner to introduce or remove heat.

In the continuous embodiment of the process according to the invention, it has proven to be useful not to add the alcohol and aqueous glyoxal in separate streams but instead to feed the above-described liquid mixture into the reactor. The liquid mixture may, for example, be prepared in a reservoir by mixing aqueous glyoxal of the desired concentration and the alcohol and also any recycled alcohol and any recycled acetal and then the mixture obtained passed into the reactor. However, the individual material streams may be passed in succession or simultaneously through devices for mixing liquids and fed into the reactor. In principle, all known devices for continuously mixing liquids such as jet mixers, static mixers and dynamic mixers are suitable. Examples of such mixers are known to those skilled in the art, for example from H. J. Hensler, "Continuous Mixing of Fluids" in Ullmann's Encyclopedia of Industrial Chemistry, $5^{th}$ ed. on CD-Rom, Wiley-VCH, Weinheim.

In a preferred embodiment of the continuous process, 60 to 75% by weight aqueous glyoxal is first prepared in the manner described above by concentrating a conventional aqueous glyoxal solution under reduced pressure and then immediately transferred into the reactor with the alcohol, which comprises both fresh alcohol and any recycled alcohol, and together with any recycled mono- and any diacetal.

It has also proven useful to recycle the alcohol removed in the workup back into the reaction, so that at least a portion of the alcohol in the mixture which is fed into the reactor results from the recycled alcohol. This may result in the mixture fed into the reactor comprising small fractions of mono- and diacetal. It is also possible to recycle the higher-boiling fractions resulting from the workup which, as well as the glyoxal monoacetal, may also contain residues of glyoxal diacetal and higher-boiling oligomers back into the continuous reaction, for example, together with the recycled alcohol. It will be appreciated that the streams are chosen in such a way that the desired alcohol/glyoxal ratio and the water content are in the ranges according to the invention.

The process according to the invention delivers the diacetals of glyoxal in high yields. Surprisingly, distilling off the water formed in the reaction is not necessary to obtain the high yields. The process according to the invention may accordingly be operated continuously in a simple manner. Separation of water and alcohol during the reaction, which would make high demands on both energy and apparatus, is not necessary.

The invention is illustrated by the following examples:

EXAMPLE 1

58 g of a 40% by weight aqueous glyoxal solution were concentrated on a rotary evaporator under reduced pressure (10 mbar). The 33.1 g of aqueous 70% glyoxal obtained and 256 g of methanol were heated to reflux with 72 g of methanol-moist, strongly acidic ion exchanger (Amberlyst®15) for 2 h. The water content of the liquid components was 2.7% by weight. The subsequent analysis by gas chromatography gave a 1,1,2,2-tetramethoxyethane content in the reaction solution of 13.6% by weight and a glyoxal dimethyl acetal content of 2.48% by weight. This corresponds to a crude yield of 65.3% of 1,1,2,2-tetramethoxyethane and of 17.2% of glyoxal dimethyl acetal, based on the glyoxal used.

EXAMPLE 2

A tubular reactor having a reaction capacity of 0.3 l and an effective length of 22 cm was charged with 219 g of ion exchanger Amberlyst®5. A solution consisting of 70% by weight aqueous glyoxal prepared as in Example 1 and methanol in a methanol:glyoxal molar ratio of 20 (glyoxal content 8%, water content 3.4% by weight) was continuously pumped through the catalyst bed at 60 ml/h in straight pass at 60° C. After a residence time of 5 h, the effluent comprises 14.5% by weight of tetramethoxyethane and 3.5% by weight of glyoxal dimethyl acetal. This corresponds to a 70% yield of tetramethoxyethane and 24.7% yield of glyoxal dimethyl acetal, based on glyoxal.

EXAMPLE 3

58 g of a 40% by weight aqueous glyoxal solution were concentrated under reduced pressure similarly to Example 1 and reacted. The 33.1 g of 70% then aqueous glyoxal obtained were heated for 24 h under reflux in 256 g of methanol with addition of 10.9 g of methanesulfonic acid (methanol:glyoxal molar ratio 20:1, initial water content 3.3% by weight). The subsequent analysis by gas chromatography gave a 1,1,2,2-tetramethoxyethane content in the reaction solution of 15.0% by weight and a glyoxal dimethyl acetal content of 2.55% by weight. This corresponds to a crude yield of 67.3% of 1,1,2,2-tetramethoxyethane and 16.5% of glyoxal dimethyl acetal, based on glyoxal.

EXAMPLE 4

58 g of a 40% aqueous glyoxal solution were concentrated under reduced pressure similarly to Example 1 and then reacted. The 33.1 g of 70% aqueous glyoxal obtained were reacted in the manner described in Example 3 in 238.9 g of methanol with addition of 10.8 g of methanesulfonic acid and 50.7 g of methyltriethylammonium methylsulfate (60% in methanol) (water content 3.0% by weight, methanol:glyoxal molar ratio=20:1). After 24 h under reflux, a solution comprising 13.91% by weight of 1,1,2,2-tetramethoxyethane and 2.69% by weight of glyoxal dimethyl acetal is obtained. This corresponds to a crude yield of 73% of 1,1,2,2-tetramethoxyethane and 20.4% of glyoxal dimethyl acetal, based on glyoxal.

EXAMPLE 5

58 g of a 40% glyoxal solution were concentrated under reduced pressure similarly to Example 1 and then reacted. The 34.2 g of 70% aqueous glyoxal obtained were heated under reflux for 24 h in 256 g of methanol with addition of 10.8 g of methanesulfonic acid and 12.4 g of methyltributylammonium methylsulfate (water content 3.3% by weight, methanol:glyoxal molar ratio=20:1). The solution obtained had a 1,1,2,2-tetramethoxyethane content of 13.8% by weight and a glyoxal dimethyl acetal content of 2.24% by weight, determined by means of gas chromatography. Crude yields of 70.9% of 1,1,2,2-tetramethoxyethane and 16.6% of glyoxal dimethyl acetal, based on glyoxal, are obtained.

EXAMPLE 6 (COMPARATIVE)

A tubular reactor (length 1 m, diameter 3.5 cm, capacity about 950 ml) was completely packed with the ion exchanger Lewatit®K2431 and flooded with methanol. A mixture of 40% by weight of glyoxal and methanol having a methanol:glyoxal molar ratio of 20:1 and a water content of 11.1% by weight was then continuously pumped into the reactor at an addition rate of 175 ml/h and through the catalyst bed at 65° C. After 28 h, the reactor effluent comprised 9% by weight of tetramethoxyethane, 5.2% by weight of glyoxal diacetal and 1% by weight of glyoxal.

This corresponds to a tetramethoxyethane yield of 44%, based on glyoxal.

EXAMPLE 7

A continuously operated falling film evaporator was used to concentrate 1678 g of a commercial 40% by weight aqueous glyoxal solution at 100 mbar to give approximately 1032 g of an approximately 65% by weight solution. The glyoxal solution obtained was immediately diluted with 5502 g of methanol (methanol:glyoxal molar ratio about 15:1, water content 5.6% by weight). This solution was pumped at an addition rate of 156 ml/h through a tubular reactor heated to 65° C. (length 1 m, diameter 3.5 cm) which was filled with 950 ml of Lewatit®K2629. After 28 h of continuous operation, the reactor effluent comprises 14% by weight of tetramethoxyethane, 5.1% by weight of glyoxal monoacetal and 0.6% by weight of glyoxal. This corresponds to a tetramethoxyethane yield of 53%, based on glyoxal.

EXAMPLE 8 (COMPARATIVE)

In a continuously operated circulation evaporator, 1273.4 g of a commercial 40% by weight glyoxal solution were concentrated at a pressure of 100 mbar to give 783.6 g of a 65% by weight aqueous glyoxal solution. The solution is immediately diluted with 2809.5 g of methanol (methanol:glyoxal molar ratio about 10:1, water content 7.7% by weight). This solution was pumped at an addition rate of 160 ml/h through the tubular reactor described in Example 7 heated to 65° C. After an operating time of 28 h, the reactor effluent comprised 15.1% by weight of tetramethoxyethane, 9.1% by weight of glyoxal monoacetal and 1.4% by weight of glyoxal. This corresponds to a tetramethoxyethane yield, based on glyoxal, of 41%.

EXAMPLE 9

In a continuously operated thin film vaporizer, 1351 g of a 40% by weight aqueous glyoxal solution were concentrated at 200 mbar to give 831.5 g of a 65% by weight solution. The solution was immediately diluted with a total of 4472 g of methanol (methanol:glyoxal molar ratio of 15:1 and water content 5.6% by weight). The solution obtained was pumped at an addition rate of 199 ml/h at ambient pressure through the reactor described in Example 7 heated to 64° C. After an operation time of 28 h, the reactor effluent comprised, inter alia, 14.4% by weight of tetramethoxyethane, 5.7% by weight of glyoxal monoacetal and 0.5% by weight of glyoxal. This corresponds to a tetramethoxyethane yield of 55%, based on glyoxal used.

In all examples, the reaction was continued until equilibrium had been achieved. The concentration of tetramethoxyethane in the reaction mixtures in all cases was above 90% of the equilibrium concentration.

We claim:

1. A process for preparing 1,1,2-tetramethoxyethane or 1,1,2,2-tetraethoxyethane by reacting from 40 to 75% by weight aqueous glyoxal with methanol or ethanol in the presence of an acid catalyst, which comprises contacting a liquid mixture which, at the beginning of the reaction, comprises the methanol or ethanol and glyoxal in a molar ratio of at least 15:1 and also water in a concentration of not more than 8% by weight with the acid catalyst until concentration in the reaction mixture of the diacetal formed reaches at least 70% of the equilibrium concentration without more than 5% by weight of the methanol or ethanol used having already been distilled off.

2. A process as claimed in claim 1, wherein from 60 to 75% by weight aqueous glyoxal is used.

3. A process as claimed in claim 1, wherein the molar ratio of alcohol to glyoxal at the beginning of the reaction is in the range from 15:1 to 30:1.

4. A process as claimed in claim 1, wherein the alcohol is methanol.

5. A process as claimed in claim 1, wherein the catalyst is selected from the group consisting of sulfuric acid, sulfuric monoesters, organic sulfonic acids and sulfonic acid ion exchange resins.

6. A process as claimed in claim 1, wherein the reaction is carried out at a temperature above 50° C.

7. A process as claimed in claim 1, wherein the reaction is carried out over a fixed bed catalyst.

8. A process as claimed in claim 1, wherein the liquid mixture additionally comprises at least one neutral or weakly acidic salt in solubilized form in a quantity of at least 1% by weight based on the mixture.

9. A process as claimed in claim 8, wherein the salt is selected from the group consisting of the sulfates, monoalkylsulfates, arylsulfonates and alkylsulfonates of metals of the first and second main group, of quaternary ammonium cations and also of FE(II) and Fe(III) ions.

10. A process as claimed in claim 1, wherein glyoxal is continuously reacted with the methanol or ethanol over a heterogeneous acid catalyst.

11. A process as claimed in claim 10, wherein a liquid mixture of from 40 to 75% by weight aqueous glyoxal and the methanol or ethanol which does not contain more than 8% by weight of water is continuously fed into a reactor which contains a heterogeneous acid catalyst and a liquid reaction mixture is continuously withdrawn from the rector which has a diacetal concentration of at least 80% of the equilibrium concentration.

12. A process as claimed in claim 11, wherein from 60 to 75% by weight aqueous glyoxal is first prepared by concentrating a conventional aqueous glyoxal solution under reduced pressure and is then fed immediately into the reactor together with the methanol or ethanol.

13. A process as claimed in claim 11, wherein the reactor has a tubular geometry.

14. A process as claimed in claim 11, wherein the mixture which is fed into the reactor comprises, in addition to the methanol or ethanol glyoxal-and water, the monoacetal and optionally, the diacetal of glyoxal.

* * * * *

UNITED STATES PATENT AND TRADEMARK OFFICE
CERTIFICATE OF CORRECTION

PATENT NO. : 6,713,656 B2
DATED : March 30, 2004
INVENTOR(S) : Heydrich et al.

It is certified that error appears in the above-identified patent and that said Letters Patent is hereby corrected as shown below:

Title page,
Item [30], insert the following:
-- [30] Foreign Application Priority Data
    Oct. 5, 2001  (DE) ..........101 49 063.1 --.

Column 10,
Line 1, "1,1,2-tetramethoxyethane" should be -- 1,1,2,2-tetramethoxyethane --.
Line 39, "FE(II)" should be -- Fe(II) --.

Signed and Sealed this

Twelfth Day of April, 2005

JON W. DUDAS
*Director of the United States Patent and Trademark Office*